United States Patent [19]

Fukuda et al.

[11] Patent Number: 5,085,854
[45] Date of Patent: Feb. 4, 1992

[54] TRANSLUCENT COSMETIC EMULSION

[75] Inventors: Morinobu Fukuda, Kanagawa; Yoshitsugu Kamata, Chiba; Masahiko Asahi, Tokyo, all of Japan

[73] Assignee: Kao Corporation, Tokyo, Japan

[21] Appl. No.: 681,424

[22] Filed: Apr. 5, 1991

Related U.S. Application Data

[63] Continuation of Ser. No. 368,511, Jun. 20, 1989, abandoned.

Foreign Application Priority Data

Jun. 20, 1988 [JP] Japan .................. 63-150191

[51] Int. Cl.$^5$ .................. A61K 7/02; A61K 7/04; A61K 7/06; A61K 7/48
[52] U.S. Cl. .................. 424/63; 424/61; 424/70; 424/73; 514/772; 514/938; 514/941
[58] Field of Search .................. 424/61, 63, 70, 73; 514/143, 148, 772, 785, 937, 938, 941

[56] References Cited

U.S. PATENT DOCUMENTS

| | | | |
|---|---|---|---|
| 4,536,519 | 8/1985 | Suzuki et al. | 514/785 |
| 4,776,976 | 10/1988 | Nakamura et al. | 514/938 X |
| 4,868,163 | 9/1989 | Takei et al. | 514/143 X |

FOREIGN PATENT DOCUMENTS

| | | | |
|---|---|---|---|
| 37161 | 10/1981 | European Pat. Off. | 514/143 |
| 0227012 | 1/1987 | European Pat. Off. | |
| 0265702 | 4/1988 | European Pat. Off. | |
| 2027047 | 2/1980 | United Kingdom | 424/70 |
| 2028133 | 3/1980 | United Kingdom | 424/70 |

Primary Examiner—Thurman K. Page
Assistant Examiner—Susan S. Rucker
Attorney, Agent, or Firm—Sughrue, Mion, Zinn, Macpeak & Seas

[57] ABSTRACT

A translucent cosmetic emulsion comprising the following components (a) to (d),
(a) a monoalkyl phosphate represented by formula (I):

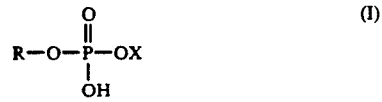

wherein R represents a β-branched alkyl group having from 8 to 36 carbon atoms; and X represents an alkali metal or an organic basic group; or a dialkyl phosphate represented by formula (II):

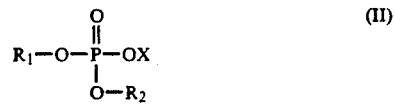

wherein $R_1$ and $R_2$ each represent a hydrocarbon group having from 10 to 24 carbon atoms; and x is as defined above;
(b) at least one nonionic surfactant, wherein the surfactant has an HLB value of from 7 to 20, and wherein when two or more nonionic surfactants are present, the surfactants together have an HLB value of from 7 to 20;
(c) an oily matrix; and
(d) water;
is disclosed. This translucent cosmetic emulsion is highly safe and remains stable upon prolonged storage.

6 Claims, No Drawings

TRANSLUCENT COSMETIC EMULSION

This is a continuation of application Ser. No. 368,511, filed June 20, 1989, now abandoned.

FIELD OF THE INVENTION

This invention relates to a translucent cosmetic emulsion. More particularly, it relates to a translucent cosmetic emulsion which is highly safe (i.e., non-irritating or non-sensitizing to skin) and remains stable upon prolonged storage.

BACKGROUND OF THE INVENTION

A translucent cosmetic emulsion having a refreshing feeling in appearance, and it is suitable to be used in summer.

A known process for the production of such a translucent cosmetic emulsion as described above, comprises, for example, adding an oily matrix to a system consisting of a nonionic surfactant, water and a polyhydric alcohol (JP-A-61-37709) (the term "JP-A" as used herein means "unexamined published Japanese patent application").

Further, a process for the production of a translucent cosmetic emulsion comprising a polyglycerol fatty acid ester and ethanol is described in JP-A-59-33206, JP-A-60-87206, JP-A-61-167609, JP-A-61-12602, JP-A-12603, JP-A-61-12604 and JP-A-61-12605; and a process for production of a translucent cosmetic emulsion comprising an oil, a nonionio surfactant, water and ethanol in a specific ratio is described in JP-A-63-132813.

However, a cosmetic obtained by this process suffers from clouding at high temperatures, the surfactant precipitates at low temperatures. Thus, the development of a translucent cosmetic emulsion which remains stable over a wide temperature range, has been urgently required.

Further, the above known cosmetic irritates a skin when a large amount of ethanol is used, or generates formalin when a large amount of a polyoxyethylene nonionic surfactant is used.

SUMMARY OF THE INVENTION

The present inventors have succeeded in the development of a translucent cosmetic emulsion which is highly safe and remains stable over a wide temperature range, by blending a specific phosphate, a nonionic surfactant having a specific HLB value, an oily matrix and water.

The term "HLB value" used herein referred to "hydrophile lipophile balance value", and the value can be determined by the method described in Griffin, *J. Soc. Cosmet. Chem.*, 1, 311 (1949).

Accordingly, the present invention provides a translucent cosmetic emulsion comprising the following components (a) to (d): (a) a monoalkyl phosphate represented by formula (I):

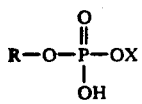

wherein R represents a β-branched alkyl group having from 8 to 36 carbon atoms; and X represents an alkali metal or an organic basic group; or a dialkyl phosphate represented by the formula (II):

wherein $R_1$ and $R_2$ represent a hydrocarbon group having from 10 to 24 carbon atoms; and X is as defined above;

(b) at least one nonionic surfactants wherein the surfactant has an HLB value of from 7 to 20, and wherein when two or more nonionic surfactants are present, the surfactants together have an HLB value of from 7 to 20;

(c) an oily matrix; and (d) water.

DETAILED DESCRIPTION OF THE INVENTION

As the monoalkyl phosphate represented by general formula (I) of the above component (a), monoalkyl phosphates as described, for example, in JP-A-58-180496 and JP-A-61-17594 (corresponding to U.S. Pat. No. 4,670,575) can be used. Among them, those wherein R is a β-branched alkyl group represented by the following formula (III), are preferred:

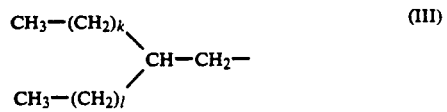

wherein k is an integer of from 2 to 18; l is an integer of from 2 to 14; and k+l is integer of from 4 to 32, preferably from 10 to 18.

In the dialkyl phosphate represented by formula (II), $R_1$ and $R_2$ each represents a hydrocarbon group having from 10 to 24 carbon atoms, preferably having from 12 to 18 carbon atoms.

Examples of alkali metals represented by X include lithium, potassium, sodium, etc., preferably potassium and sodium; and organic bases represented by X include basic amino acids such as arginine, ornithine, lysine and oxylidine, and alkanolamines having hydroxyalkyl group(s) having two or three carbon atoms such as triethanolamine and monoethanolamine. Among them, arginine is more preferred as an organic base.

Preferred examples of the monoalkyl phosphates represented by general formula (I) include L arginine mono 2-hexyldodecylphosphate, L-arginine mono 2-octyldodecyl phosphate, L-arginine mono 2-decyltetradecylphosphate, and the like.

Preferred example of the dialkyl phosphates represented by general formula (II) include L-arginine dilaurylphosphate, L-arginine dimyristylphosphate, L-arginine dicetylphosphate, and the like.

The monoalkyl phosphates represented by general formula (I) and the dialkyl phosphates represented by general formula (II) can be used either alone or as a mixture of two or more of them.

Suitable nonionic surfactant(s) of component (b), include not only those capable of giving an HLB value of from 7 to 20 alone but also a mixture of a nonionic surfactant having an HLB value less than 7 with a nonionic surfactant having an HLB value of 7 or above, which gives a total HLB value of from 7 to 20.

Examples of nonionic surfactants capable of giving an HLB value of from 7 to 20 alone include polyoxyethylene hardened castor oil, polyoxyethylene sorbitan fatty acid esters, polyoxyethylene alkyl ethers, polyoxyethylene alkyl phenyl ethers, polyoxyethylene fatty acid esters, polyoxyethylene glycerol fatty acid esters, polyglycerol alkyl ethers and polyglycerol alkyl phenyl ethers. Among these nonionic surfactants, polyoxyethylene (polymerization degree: 20 to 80) hardened castor oil and polyoxyethylene (polymerization degree: 10 to 30) monoisostearate are preferred.

Examples of nonionic surfactants having an HLB value less than 7 include monoglycerol alkyl ethers, sorbitan fatty acid esters, glycerol fatty acid esters and sucrose fatty acid esters. These nonionic surfactants may be preferably used in the present invention together with polyoxyethylene (polymerization degree: 20 to 80), hardened castor oil, polyoxyethylene (polymerization degree: 10 to 30), sorbitan monoisostearate, sorbitan monoisostearate or monoglycerol monoisostearyl ether.

Examples of the oily matrix of the component (c) include hydrocarbons such as squalane, liquid paraffin, vaseline and ceresin; ester oils such as jojoba oil and octyldodecyl myristate; glycerides such as olive oil, macadamia nut oil and diacylglycerol; silicone oils; higher fatty acids and higher alcohols. Among them, oily matrix having not high polarity are preferred. These oily matrix can be used either alone or as a mixture of two or more of them.

The translucent cosmetic emulsion of the present invention may be produced in a conventional manner. Preferably, it is obtained by mixing and stirring components (a), (b) and (c) together, to thereby give a homogeneous mixture. Component (d) is then added thereto.

In the case of that one or more of components (a), (b) and (c) is/are a solid at room temperature even in the presence of water, a homogeneous mixture can be obtained by mixing and stirring the mixture after melting the component(s) by heating. In the case of that the mixture of components (a), (b) and (c) separating into two or more phases, the mixture must be sufficiently mixed and stirred.

A preferable composition of the translucent cosmetic emulsion of the present invention is as follows.

|  | Content (% by weight) | Preferable content (% by weight) |
| --- | --- | --- |
| Component (a) | 0.005–1 | 0.01–0.5 |
| Component (b) | 0.1–5 | 1–3 |
| Component (c) | 0.5–10 | 1–5 |
| Component (d) | 25–95 | 40–90 |

In addition to the above components (a) to (d), the translucent cosmetic emulsion of the present invention may further comprise 1 to 30 % by weight, preferably 3 to 20 % by weight of a polyhydric alcohol humectant such as glycerol, propylene glycol, 1,3-butylene glycol or dipropylene glycol as a component (e). Component (e) is effective in maintaining the translucency of the cosmetic emulsion. In this case, components (a), (b), (c) and (e) are mixed together to thereby give an isotropic solution and then the component (d), namely, water is added thereto. Thus, a translucent cosmetic emulsion having high stability can be obtained.

In addition to the above components, the translucent cosmetic emulsion of the present invention may further comprise various cosmetic components commonly employed in the art, such as UV absorbers, lower alcohols, chelating agents, pH adjusters, preservatives, thickners, dyes and perfumes, so long as they would not adversely effect the translucent property of the emulsion of the present invention. It is particularly preferable to use 3 to 30 % by weight, more preferably 5 to 15 % by weight of ethanol, since a refreshing feeling can be obtained thereby.

The translucent cosmetic emulsion of the present invention may be formulated into various forms including lotions such as a softening lotion, after-shaving lotion and a transparent makeup- lotion; skin cosmetics such as summer milky lotion; and hair cosmetics such as hair tonic and hair liquid.

In the present invention, the term "translucent" means those having a turbidity of 1 to 90 ppm determined according to determination with turbidimeter with integrating sphere, on a pure kaolin basis (provided by JIS-K1010, 8). In general, a transparent cosmetic such as a cosmetic lotion has a turbidity of 1 ppm or below while a clouded emulsion such as a milky lotion has a turbidity of 90 ppm or above. Thus the translucent emulsion cosmetic of the present invention lies between them. The emulsion particle size of the translucent cosmetic emulsion of the present invention is approximately from 10 to 200 nm.

The translucent cosmetic emulsion of the present invention is highly safe and remains stably translucent over a wide temperature range of $-10°$ to $50°$ C. for a prolonged period of time, without showing any precipitation, separation nor clouding. Thus it has a refreshing appearance.

The present invention is now illustrated in greater detail by references to the following Examples which, however, are not to be construed as limiting the present invention in any way.

EXAMPLE 1

(i) A summer milky lotion having the following composition was produced in the following manner.

Preparation process:

Components (1) to (10) were mixed together and dissolved by heating. The oily phase thus obtained was maintained at 70° C. Separately, components (11) and (13) were heated and the aqueous phase thus obtained was maintained at 70° C. Then the aqueous phase was added to the oily phase and the mixture was emulsified in an emulsifying machine. The obtained emulsion was cooled to 30° C. and then perfume (12) was added thereto. After filtering, a milky lotion of the present invention (products of invention 1 to 3) and comparative products (comparative products 1 to 3) were obtained.

TABLE 1

|  | Comparative Product 1 | Comparative product 2 | Comparative product 3 | Product of invention 1 | Product of invention 2 | Product of invention 3 |
| --- | --- | --- | --- | --- | --- | --- |
| (1) Squalane | 2.0 | 2.0 | 2.0 | 2.0 | 2.0 | 2.0 |
| (2) Sorbitan monoisostearate (HLB 5.0) | — | 1.0 | 1.0 | — | 1.0 | 1.0 |
| (3) Polyoxyethylene sorbitan monooleate (6 E.O., HLB 10.0) | 2.0 | — | — | 2.0 | — | — |

TABLE 1-continued

| | Comparative Product 1 | Comparative product 2 | Comparative product 3 | Product of invention 1 | Product of invention 2 | Product of invention 3 |
|---|---|---|---|---|---|---|
| (4) Polyoxyethylene sorbitan monoisostearate (20 E.O., HLB 15.0) | — | 1.0 | 1.0 | — | 1.0 | 1.0 |
| (5) L-Arginine cetylphosphate | 0.2 | — | 0.2 | — | — | — |
| (6) L-Arginine 2-hexyldecylphosphate | — | — | — | 0.2 | 0.2 | — |
| (7) L-Arginine dicetylphosphate | — | — | — | — | — | 0.2 |
| (8) Glycerol | 4.0 | 4.0 | 4.0 | 4.0 | 4.0 | 4.0 |
| (9) 1,3-Butylene glycol | 2.0 | 2.0 | 2.0 | 2.0 | 2.0 | 2.0 |
| (10) Methylparaben | 0.1 | 0.1 | 0.1 | 0.1 | 0.1 | 0.1 |
| (11) Ethanol | 10.0 | 10.0 | 10.0 | 10.0 | 10.0 | 10.0 |
| (12) Perfume | 0.1 | 0.1 | 0.1 | 0.1 | 0.1 | 0.1 |
| (13) Purified water | balance | balance | balance | balance | balance | balance |
| Total (% by weight) | 100 | 100 | 100 | 100 | 100 | 100 |

(ii) The stability upon storage of the summer milky lotion produced in (i) above, was evaluated. The results are shown in Table 2. Table 2 indicates that each of the products of invention 1 to 3 showed a small change in turbidity depending on temperature and thus maintained high translucency after being stored for a long period of time, compared with the comparative products 1 to 3.

TABLE 2

| | Comparative product 1 | Comparative product 2 | Comparative product 3 | Product of invention 1 | Product of invention 2 | Product of invention 3 |
|---|---|---|---|---|---|---|
| Turbidity (ppm) | | | | | | |
| −5° C. | 20.0 | 20.8 | 19.3 | 19.8 | 18.6 | 20.1 |
| room temp. | 23.7 | 44.3 | 24.6 | 20.7 | 20.4 | 21.4 |
| 50° C. | 110.5 | 152.7 | 103.5 | 27.5 | 26.2 | 32.3 |
| Appearance (After storage at 40° C. for 3 months) | clouding | clouding | clouding | translucent | translucent | translucent |

EXAMPLE 2

Preparation of cosmetic lotion:

| | Composition Component | Amount (% by weight) |
|---|---|---|
| Oily phase: | myristate isostearate diglyceride | 4.0 |
| | stearic acid | 0.1 |
| | polyoxyethylene hardened castor oil (40 E.O., HLB 12.5) | 3.0 |
| Aqueous phase: | L-arginine dicetylphosphate | 0.3 |
| | glycerol | 15.0 |
| | 1,3-butylene glycol | 5.0 |
| | polyethylene glycol 1500 | 2.0 |
| | methylparaben | 0.3 |
| | xanthane gum | 0.3 |
| | perfume | 0.1 |
| | purified water | balance |
| | Total | 100 |

The above oily phase components were mixed together and dissolved by heating. The oily phase thus obtained was maintained at 70° C. The abovementioned aqueous phase components were similarly mixed by heating at 70° C. Then, the obtained aqueous phase was added to the oily phase and the obtained mixture was emulsified in an emulsifying machine. The resulting emulsion was cooled to a final temperature of 30° C. and then filtered. Thus, a cosmetic lotion (product of the invention 4) was obtained.

EXAMPLE 3

Preparation of softening lotion:

| | Composition Component | Amount (% by weight) |
|---|---|---|
| Oily phase: | jojoba oil | 1.0 |
| | vaseline | 0.1 |
| | polyoxyethylene octyl dodecyl ether (20 E.O., HLB 11.0) | 1.0 |
| Aqueous phase: | L-arginine 2-hexyldecyl-phosphate | 0.1 |
| | glycerol | 7.0 |
| | 1,3-butylene glycol | 3.0 |
| | methylparaben | 0.1 |
| | ethanol | 7.0 |
| | perfume | 0.1 |
| | purified water | balance |
| | Total | 100 |

The above oily phase components were mixed together and dissolved by heating. The oily phase thus obtained was maintained at 70° C. The aqueous phase components were similarly mixed by heating to 70° C. The aqueous phase thus obtained was added to the oily phase and the resulting mixture was emulsified with an emulsifying machine. The obtained emulsion was cooled to a final temperature of 30° C. and filtered. Thus, a cosmetic lotion (product of the invention 5) was obtained.

EXAMPLE 4

Preparation of hair tonic:

| | Composition Component | Amount (% by weight) |
|---|---|---|
| Oily phase: | olive oil | 3.0 |
| | polyoxyethylene oleyl ether (25 E.O., HLB 17.5) | 1.0 |
| Aqueous phase: | L-arginine dilaurylphosphate | 0.1 |
| | propylene glycol | 10.0 |
| | l-menthol | 0.01 |
| | isopropylmethylphenol | 0.1 |
| | ethanol | 40.0 |
| | perfume | 0.1 |

| Composition | | |
|---|---|---|
| Component | | Amount (% by weight) |
| purified water | | balance |
| | Total | 100 |

The above oily phase components were mixed together and dissolved by heating. The oily phase thus obtained was maintained at 70° C. The aqueous phase components were similarly mixed by heating to 70° C. The aqueous phase thus obtained was added to the oily phase and the resulting mixture was emulsified with an emulsifying machine. The obtained emulsion was cooled to a final temperature of 30° C. and filtered. Thus, a hair tonic (product of the invention 6) was obtained.

Each of the products of the present invention 4 to 6, prepared in the above Examples 2 to 4 respectively, was a translucent emulsion cosmetic which was highly safe and remained stable upon prolonged storage.

EXAMPLE 5

Preparation of milky lotion:

| Composition | | |
|---|---|---|
| | Component | Amount (% by weight) |
| (1) | squalane | 2.0 |
| (2) | sorbitan monostearate (HLB 4.7) | 1.0 |
| (3) | polyoxyethylene (20 E.O.) sorbitan monostearate (HLB 14.9) | 1.0 |
| (4) | L-arginine 2-hexyldecylphosphate | 0.1 |
| (5) | glycerol | 3.0 |
| (6) | 1,3-butylene glycol | 2.0 |
| (7) | butylparaben | 0.1 |
| (8) | ethanol | 15.0 |
| (9) | perfume | 0.1 |
| (10) | purified water | balance |
| | Total | 100 |

Preparation process 1:

The oily phase components (1), (2) and (3) were mixed together and dissolved by heating. The oily phase thus obtained was maintained at 70° C. The aqueous phase components (4), (5), (6), (7), (8), (9) and (10) were similarly mixed by heating to 70° C. The aqueous phase thus obtained was added to the oily phase and the resulting mixture was emulsified with an emulsifying machine. The obtained emulsion was cooled to a final temperature of 30° C. and filtered. Thus, a milky lotion (product of the invention 7) was obtained.

Preparation process 2:

The above-mentioned components, (1), (2), (3), (4), (5), (6) and (7) were thoroughly mixed together at 70° C. and maintained at this temperature. Components (8), (9) and (10) were similarly mixed at 70° C. The aqueous phase thus obtained was added to the above oily phase and the resulting mixture was emulsified with an emulsifying machine. The emulsion thus obtained was cooled to a final temperature of 30° C. and then filtered. Thus, a milky lotion (product of the invention 8) was obtained.

The products of the invention 7 and 8 thus prepared were stored for three months. The emulsion particle size and appearance of each product were evaluated. The results are shown in Table 3. Table 3 indicates that the translucent appearance of each product showed no change; and that the product of invention 7 showed a slight increase in the emulsion particle size after being stored at 40° C. while the product of the invention 8 scarcely showed any change.

TABLE 3

| | Product 7 | Product 8 |
|---|---|---|
| Appearance (After storage at 40° C. for 3 months) | translucent | translucent |
| Emulsion particle size (nm) | | |
| After storage at room temperature for 3 months | 43 | 45 |
| After storage at 40° C. for 3 months | 60 | 47 |

While the invention has been described in detail and with reference to specific embodiments thereof, it will be apparent to one skilled in the art that various changes and modifications can be made therein without departing from the spirit and scope thereof.

What is claimed is:

1. A translucent cosmetic emulsion having an emulsion particle size of approximately from 10 to 200 nm comprising the following components (a) to (d):

(a) a monoalkyl phosphate represented by formula (I):

wherein

R represents a β-branched alkyl group having from 8 to 36 carbon atoms; and x represents an alkali metal or an organic basic group; or a dialkyl phosphate represented by formula (II):

wherein $R_1$ and $R_2$ each represent a hydrocarbon group having from 10 to 24 carbon atoms; and X is as defined above;

(b) at least one nonionic surfactant, wherein said surfactant has an HLB value of from 7 to 20, and wherein when two or more nonionic surfactants are present, said surfactants together have an HLB value of from 7 to 20;

(c) an oily matrix, wherein said oily matrix represents a member selected from the group consisting of hydrocarbons, ester oils, glycerides, silicone oils, higher fatty acids and higher alcohols; and (d) water, wherein component (a) is present in an amount of from 0.005 to 1.00% by weight; component (b) is present in an amount of from 0.1 to 5.0% by weight; component (c) is present in an amount of from 1.0 to 5.0% by weight; and component (d) is present in an amount of from 40.00 to 90.0% by weight.

2. A translucent cosmetic emulsion according to claim 1, wherein $R_1$ and $R_2$ each represents a hydrocarbon group having form 12 to 18 carbon atoms.

3. A translucent cosmetic emulsion according to claim 1, wherein component (a) is present in an amount of from 0.01 to 0.5% by weight and; component (b) is present in an amount of from 1.0 to 3.0 by weight.

4. A translucent cosmetic emulsion according to claim 1, wherein R represents a β-branched alkyl group of formula (III):

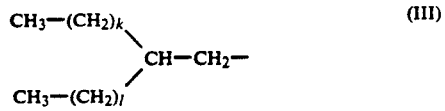

(III)

wherein k is an integer of from 2 to 18; l is an integer of from 2 to 14; and k+l is an integer of from 4 to 32.

5. A translucent cosmetic emulsion according to claim 4, wherein k+l is an integer of from 10 to 18.

6. A translucent cosmetic emulsion according to claim 1, wherein said emulsion is prepared by a process comprising the steps of:
   mixing and stirring said components (a), (b) and (c) to obtain a homogenous mixture; and
   adding said component (d) to the homogenous mixture.

* * * * *